Figures 1, 2:
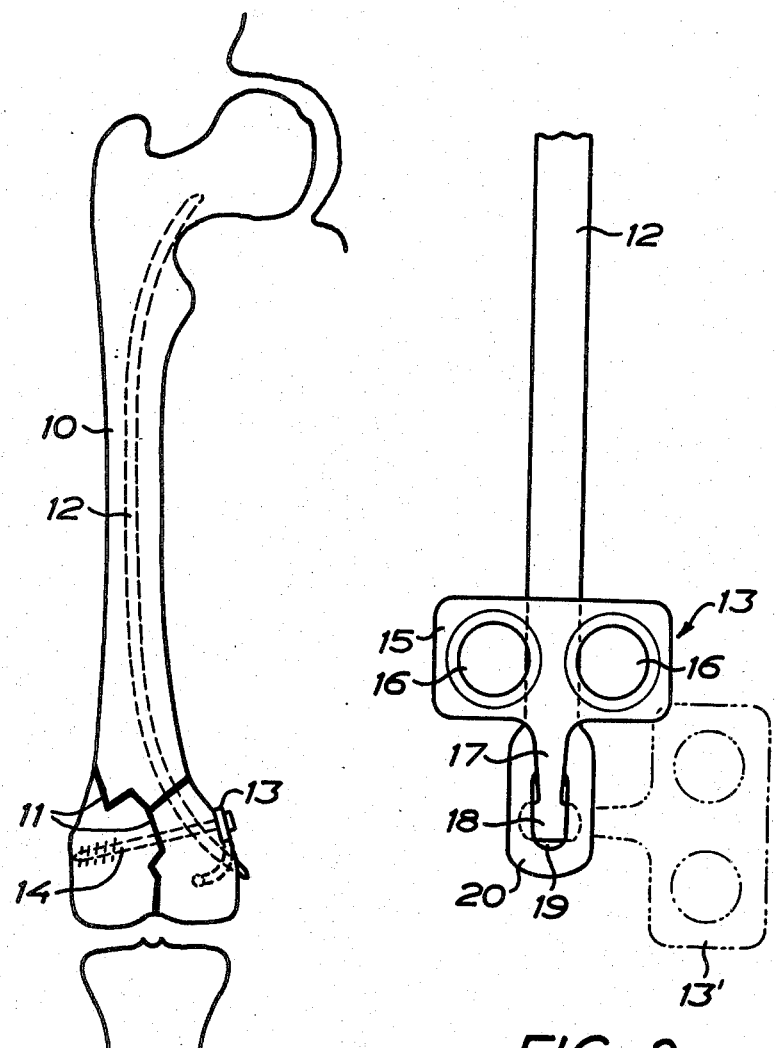

United States Patent [19]

Kolmert

[11] Patent Number: 4,473,069

[45] Date of Patent: Sep. 25, 1984

[54] DEVICE FOR INTERCONNECTING AN ELASTIC NAIL AND A CROSS SCREW

[76] Inventor: Lars Kolmert, Leifs väg 73, S-237 00 Bjärred, Sweden

[21] Appl. No.: 398,014

[22] Filed: Jul. 14, 1982

[30] Foreign Application Priority Data

Jul. 17, 1981 [SE] Sweden .................................. 8104424

[51] Int. Cl.³ .......................... A61F 5/04; A61B 17/18
[52] U.S. Cl. ............................... 128/92 B; 128/92 BA; 128/92 BC; 128/92 D
[58] Field of Search .............. 128/92 B, 92 BC, 92 R, 128/92 BA, 92 E, 92 D, 92 G

[56] References Cited

U.S. PATENT DOCUMENTS 4,055,172 10/1977 Ender et al. ................... 128/92 BC
4,227,518 10/1980 Aginsky ......................... 128/92 BC

FOREIGN PATENT DOCUMENTS 576249 6/1976 Sweden .......................... 128/92 BC
825042 5/1981 U.S.S.R. ............................. 128/92 E Primary Examiner—Ronald L. Frinks

[57] ABSTRACT

A device for interconnecting an elastic nail and a cross screw for the fixation of bone fractures. The device comprises as a separate element a coupling piece with a plate portion which can be mounted to the outside of the bone by means of one or more cross screws. A coupling hook projects from the plate portion, which forms a cross head and can be brought to engage lockingly the elastic nail by the cross head being passed through a slot in one end of the nail and being rotated.

6 Claims, 4 Drawing Figures

U.S. Patent  Sep. 25, 1984  Sheet 1 of 2  4,473,069

DEVICE FOR INTERCONNECTING AN ELASTIC NAIL AND A CROSS SCREW

The present invention relates to a device for interconnecting an elastic nail and a cross screw in the fixation of bone fractures. It has come about particularly for the fixation of fractures in the lower third of the femur.

From a surgical point of view the femur can be divided into three parts. As far as the upper and intermediate thirds are concerned there are today in most cases good possibilities of fixation while the lower third, however, presents problems as to the fixation of the fractures that can occur therein, viz. unicondylar fractures wherein one condyle has been burst off, bicondylar fractures wherein both condyles are displaced, and supracondylar fractures wherein the fracture does not extend intercondylarly. In the lower third of the femur pre-drilling and Kütscher-nailing no longer provides a stable fixation. For fixation in this part of the femur so-called angle condylar plates are used which function well in a stable skeleton but on the other side do not provide a satisfactory fixation when the skeleton is weakened (fragile). This is most often the case as far as older persons are concerned where this fracture most frequently occurs and the fixation by means of angle condylar plates will be too rigid; a fragile skeleton calls for a more flexible fixation.

In an effort to provide an improved fixation in the lower part of the femur the Zickel-nail has been used. This nail is a medullary nail formed as a leaf spring, which has a rigid distal end, formed with openings, which can be fixed in the condylar portion by means of a cross screw also the condyle of the other side being fixed. Owing to the cross screw the nail is prevented from changing the position thereof. However, it has been found that this nail in the fixation of supracondylar fractures may cause further fractures and that it is difficult to provide a satisfactory fixation due to the leaf spring form of the nail. The convex side of the nail is in fact turned slightly backwards while the natural curvature of femur is convex forwards. Moreover, the rather rigid nail may keep the condylar portion apart to a greater extent than that desired. As a consequence thereof this portion may be projected in relation to the proximal fragment an the separate condyles may be twisted.

On the basis of the experiences thus obtained when available means for the fixation of bone fractures have been used in case of fractures in the lower third of the femur the following objects desired can be listed as far as patients with bone fragility are concerned.

1. Medullary nails should be used instead of an angle condylar plate with screws.
2. The nail should have a sufficient elasticity and a round cross-sectional form in order to avoid stress dislocation or further fractures.
3. It should be possible to utilize the total length of the medullary cavity.
4. It should be possible to lock the bone fragments at the upper end of the femur against twisting by means of two nails, one from each condyle, in connection with fractures in the lower part of the femur.
5. Where an artificial bone has been inserted previously or a fracture fixation in the upper part of the femur has been made earlier it should be possible to use also shortened nails.
6. There should be the possibility of locking against twisting also in the condylar portion in the lower end of the femur.
7. The nail should be prevented from disengaging the lower part of the femur.
8. It should be possible to keep together displaced condyles.

In order to achieve these objects in treating fractures in the lower third of the femur with the aim of attaining an early mobilization of the patient from bed and possibly also a rapid weight-bearing while providing a fixation which is less rigid than that obtained by means of an angle condylar plate but is more stable than that obtained only by an external fixation with plaster or other articulated bandage, it is proposed according to the invention a device for interconnecting an elastic nail and a cross screw in the fixation of bone fractures comprising as a separate element a coupling piece forming a plate portion to be fixed by means of at least one cross screw, and a coupling hook projecting from said portion and forming a cross head to be inserted through a slot in the end portion of the nail and be rotated so as to lockingly engage the elastic nail.

Preferably, the elastic nail is of a type similar to the Ender-nail as presently constructed since this nail satisfies the objects according to items 1 to 4 listed above. It has a moderate elasticity and a favourable form. Moreover, the use thereof in the upper part of the femur of older persons having bone fragility, is well experienced. The nail can be shortened without any inconvenience so as to satisfy the object of item 5. The objects of the other items are satisfied by the nail being anchored by means of the coupling piece according to the invention.

An important advantage of the device according to the invention is also to be seen in the fact that the elastic nails as well as the cross screws, screwed into the spongy porous part of the bone (cancellous screws) already today are used in most departments for fracture surgery. Therefore, the device can be used by applying surgical utensiles now available.

Figure 3:
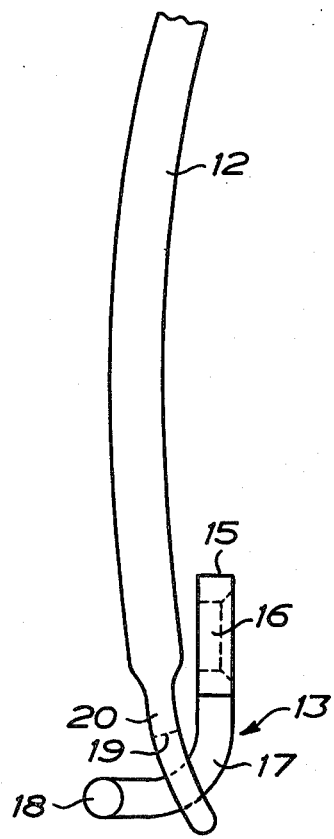
Figure 4:
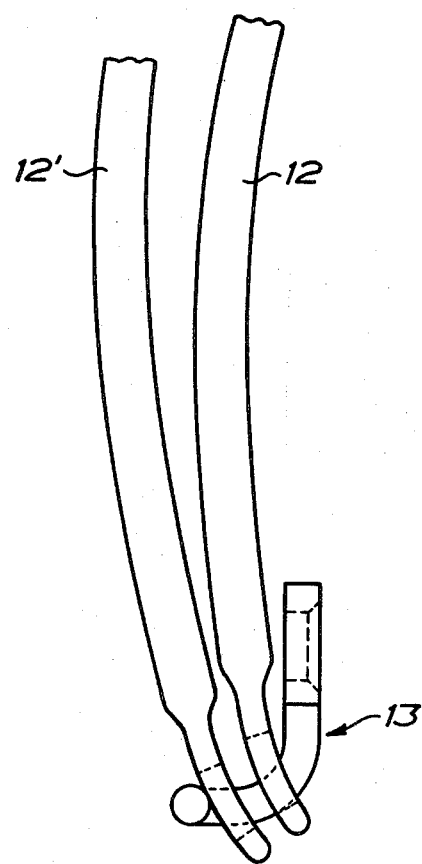

In order to illustrate the invention it will be described in more detail below with reference to the acompanying drawing in which FIG. 1 is a side view of the device according to the invention applied to a femur having a bicondylar fracture in the lower end thereof, said fracture being fixed by using an elastic nail and cancellous screws interconnected by means of the device according to the invention, FIG. 2 is an enlarged front view of the device according to the invention the elastic nail being fragmentarily shown, FIG. 3 is a side view of the device in FIG. 2, and FIG. 4 is a side view similar to FIG. 3 showing two elastic nails.

With reference to FIG. 1 a femur 10 having a bicondylar fracture 11 at the lower end of the femur is shown. In order to fix this fracture an elastic nail 12 of a construction known per se is driven from the side into the femur from the lower end thereof through one condyle and then through the medulla into th eupper end of the femur. The nail 12 is anchored in the lower end of the femur by means of a coupling piece 13 connected to said one condyle by means of cancellous screws 14 of a type known per se, which at the same time keep the displaced condyles together. Another elastic nail shall be driven into the femur from the other condyle and shall be fixed in the manner described, but this is not shown in FIG. 1 in order not to make the drawing unnecessarily complicated.

The coupling piece 13 is shown in more detail in FIGS. 2 and 3 to which reference is made. It is formed as an integral element of stainless steel and comprises a rectangular plate 15 having two circular openings 16 countersunk at one side of the plate, to receive therein the screws 14. From the centre of one of the longer edges of the plate a coupling hook 17 extends in the plane of the plate and then curves outwards at 90° to terminate at the outer end thereof in a cross head 18. When the elastic nail has been driven into the femur the cross head can be passed through a longitudinal slot 19 in a flattened end portion 20 of the projecting lower end of the nail when the coupling piece 13 is in the position indicated by dash-and-dot lines 13′ in FIG. 2. Then, by rotating the coupling piece 13 to the position shown by solid lines in FIG. 2, i.e. over 90°, the coupling hook is brought to engage lockingly the nail so as to fixedly retain the nail, the cross head 18 being positioned transversely of the slot 19. The coupling piece can now be fixed by means of the cancellous screws 14 on the outside of the femur as shown in FIG. 1. When this is done there are generous possibilities of adjusting the location of the coupling piece such that it will be located in the best manner considering the actual fracture, and the screws will be oriented as desired. It is particularly advantageous that the coupling piece if desired can be located on the condyle above the knee joint proper. It is also advantageous that the nail first can be driven into the femur and the coupling piece then can be mounted such that the mounting to a minor extent will be dependent on the location of the nail in the femur. A further advantage is that a further nail 12′ can be anchored in the lower end of the femur by means of a single coupling piece 13 as shown in FIG. 4.

With two elastic nails inserted one from each condyle, the bone fragments can be locked against twisting at the upper end of the femur by the two nails. The nail provides a flexible fixation of the fracture and is prevented from sliding out of the femur by the coupling piece which also locks against twisting in the lower fragment.

I claim:

1. A device for the fixation of fractures in the lower femur bone, comprising, in combination:
(a) at least one elastic nail for passing through the bone across the fracture; the nail having one end for projecting beyond the bone, with a hook-receiving aperture through the projecting end;
(b) a coupling member formed with
 (i) a plate portion having at least one aperture therethrough, for receiving a cross screw to be anchored in the bone;
 (ii) a coupling hook projecting from the plate portion and so oriented with respect to the plate portion that the hook can be inserted through the nail aperture before the plate portion is anchored in the bone, but cannot be withdrawn from the nail aperture after the plate portion is anchored to the bone; and
(c) at least one screw for anchoring the plate portion to the bone; whereby the elastic nail is adapted to be locked in place in the bone by the coupling hook when the coupling member is itself anchored to the bone by the screw, and is free to move at the aperture along the coupling hook.

2. A device according to claim 1 wherein the coupling hook extends from an edge of the plate portion.

3. A device according to claim 2 wherein the coupling hook extends from the edge substantially in the plane of the plate portion, and then curves in the hook portion from that plane to a plane substantially perpendicular thereto.

4. A device according to claim 1 wherein the projecting end of the elastic nail is flattened, with the aperture through the flattened projecting end.

5. A device according to claim 1 wherein there are two elastic nails, both to be locked in place by the coupling member, and two screws for anchoring the plate portion of the coupling member to the bone.

6. A device according to claim 1 in which the coupling hook is so oriented with respect to the plate portion that rotation of the plate portion through 90° moves the coupling hook from the position at which the nail can be inserted to the position in which the plate portion is anchored in the bone.

* * * * *